(12) United States Patent
Andrade et al.

(10) Patent No.: US 10,819,100 B1
(45) Date of Patent: Oct. 27, 2020

(54) CARBON MONOXIDE DETECTOR AND SHUTOFF SYSTEM

(71) Applicants: Jose Andrade, Toronto (CA); Antonio Andrade, Toronto (CA)

(72) Inventors: Jose Andrade, Toronto (CA); Antonio Andrade, Toronto (CA)

( * ) Notice: Subject to any disclaimer, the term of this patent is extended or adjusted under 35 U.S.C. 154(b) by 177 days.

(21) Appl. No.: 16/149,209

(22) Filed: Oct. 2, 2018

(51) Int. Cl.
| | |
|---|---|
| *H02H 5/00* | (2006.01) |
| *H01R 31/06* | (2006.01) |
| *G01N 33/00* | (2006.01) |
| *H02H 1/00* | (2006.01) |
| *H01H 47/22* | (2006.01) |
| *H03F 3/45* | (2006.01) |

(52) U.S. Cl.
CPC ............. *H02H 5/00* (2013.01); *G01N 33/004* (2013.01); *H01H 47/22* (2013.01); *H01R 31/065* (2013.01); *H02H 1/0007* (2013.01); *H03F 3/45475* (2013.01)

(58) Field of Classification Search
CPC .......... H02H 5/00; H02H 1/0007; H02H 1/00; G01N 33/004; G01N 33/00; H01H 47/22; H01R 31/065; H01R 31/06; H02F 3/45475; H03F 3/45; H03F 3/45475
See application file for complete search history.

(56) References Cited

U.S. PATENT DOCUMENTS

| | | |
|---|---|---|
| D308,646 S | 6/1990 | Grilk |
| 6,339,379 B1 | 1/2002 | Argus et al. |
| 6,989,757 B2 | 1/2006 | Winters |
| 7,033,165 B1 | 4/2006 | Brown |
| 7,746,240 B2 | 6/2010 | Vij |
| 7,898,427 B1 | 3/2011 | Kim |
| 2002/0125877 A1* | 9/2002 | Cooke ..................... G01R 15/18 324/127 |
| 2005/0168901 A1* | 8/2005 | Dayoub ................. G08B 17/10 361/115 |
| 2008/0180260 A1 | 7/2008 | Shirlee |
| 2010/0201531 A1* | 8/2010 | Pakravan ............... G08B 29/20 340/632 |

FOREIGN PATENT DOCUMENTS

CA 2272116 11/2000

* cited by examiner

*Primary Examiner* — Robert L Deberadinis (57) ABSTRACT

The carbon monoxide detector and shutoff system is an electrical switching device. The carbon monoxide detector and shutoff system inserts into an electrical connection between the national electric grid and an electrical load. The carbon monoxide detector and shutoff system senses the carbon monoxide concentration within the atmosphere. Should the detected concentration of carbon monoxide exceed a threshold level, the carbon monoxide detector and shutoff system interrupts the circuit between the national electric grid and the electrical load. The carbon monoxide detector and shutoff system comprises a pass-through circuit, a control circuit, and a housing. The housing contains the pass-through circuit and the control circuit. The pass-through circuit inserts a relay between the national electric grid and the electrical load. The control circuit is an electrical circuit that opens and closes the relay in response to the detected concentration of carbon monoxide.

15 Claims, 5 Drawing Sheets

CARBON MONOXIDE DETECTOR AND SHUTOFF SYSTEM

CROSS REFERENCES TO RELATED APPLICATIONS

Not Applicable

STATEMENT REGARDING FEDERALLY SPONSORED RESEARCH

Not Applicable

REFERENCE TO APPENDIX

Not Applicable

BACKGROUND OF THE INVENTION

Field of the Invention

The present invention relates to the field of instruments including alarm systems, more specifically, a cutoff system actuated by the detection of a specific gas. (G08B17/117)

SUMMARY OF INVENTION

The carbon monoxide detector and shutoff system is an electrical switching device. The carbon monoxide detector and shutoff system inserts into an electrical connection between the national electric grid and an electrical load. The carbon monoxide detector and shutoff system senses the carbon monoxide concentration within the atmosphere. Should the detected concentration of carbon monoxide exceed a threshold level, the carbon monoxide detector and shutoff system interrupts the circuit between the national electric grid and the electrical load. The carbon monoxide detector and shutoff system comprises a pass-through circuit, a control circuit, and a housing. The housing contains the pass-through circuit and the control circuit. The pass-through circuit inserts a relay between the national electric grid and the electrical load. The control circuit is an electrical circuit that opens and closes the relay in response to the detected concentration of carbon monoxide.

These together with additional objects, features and advantages of the carbon monoxide detector and shutoff system will be readily apparent to those of ordinary skill in the art upon reading the following detailed description of the presently preferred, but nonetheless illustrative, embodiments when taken in conjunction with the accompanying drawings.

In this respect, before explaining the current embodiments of the carbon monoxide detector and shutoff system in detail, it is to be understood that the carbon monoxide detector and shutoff system is not limited in its applications to the details of construction and arrangements of the components set forth in the following description or illustration. Those skilled in the art will appreciate that the concept of this disclosure may be readily utilized as a basis for the design of other structures, methods, and systems for carrying out the several purposes of the carbon monoxide detector and shutoff system.

It is therefore important that the claims be regarded as including such equivalent construction insofar as they do not depart from the spirit and scope of the carbon monoxide detector and shutoff system. It is also to be understood that the phraseology and terminology employed herein are for purposes of description and should not be regarded as limiting.

BRIEF DESCRIPTION OF DRAWINGS

The accompanying drawings, which are included to provide a further understanding of the invention are incorporated in and constitute a part of this specification, illustrate an embodiment of the invention and together with the description serve to explain the principles of the invention. They are meant to be exemplary illustrations provided to enable persons skilled in the art to practice the disclosure and are not intended to limit the scope of the appended claims.

DETAILED DESCRIPTION OF THE EMBODIMENT

The following detailed description is merely exemplary in nature and is not intended to limit the described embodiments of the application and uses of the described embodiments. As used herein, the word "exemplary" or "illustrative" means "serving as an example, instance, or illustration." Any implementation described herein as "exemplary" or "illustrative" is not necessarily to be construed as preferred or advantageous over other implementations. All of the implementations described below are exemplary implementations provided to enable persons skilled in the art to practice the disclosure and are not intended to limit the scope of the appended claims. Furthermore, there is no intention to be bound by any expressed or implied theory presented in the preceding technical field, background, brief summary or the following detailed description.

Detailed reference will now be made to one or more potential embodiments of the disclosure, which are illustrated in FIGS. 1 through 5.

The carbon monoxide detector and shutoff system 100 (hereinafter invention) is an electrical switching device. The invention 100 inserts into an electrical connection between the national electric grid 114 and an electrical load 115. The invention 100 senses the carbon monoxide concentration within the atmosphere. Should the detected concentration of carbon monoxide exceed a threshold level, the invention 100 interrupts the circuit between the national electric grid 114 and the electrical load 115. The invention 100 comprises a pass-through circuit 101, a control circuit 102, and a housing 103. The housing 103 contains the pass-through circuit 101 and the control circuit 102. The pass-through circuit 101 inserts a relay 111 between the national electric grid 114 and the electrical load 115. The control circuit 102 is an electrical circuit that opens and closes the relay 111 in response to the detected concentration of carbon monoxide.

Figure 5:
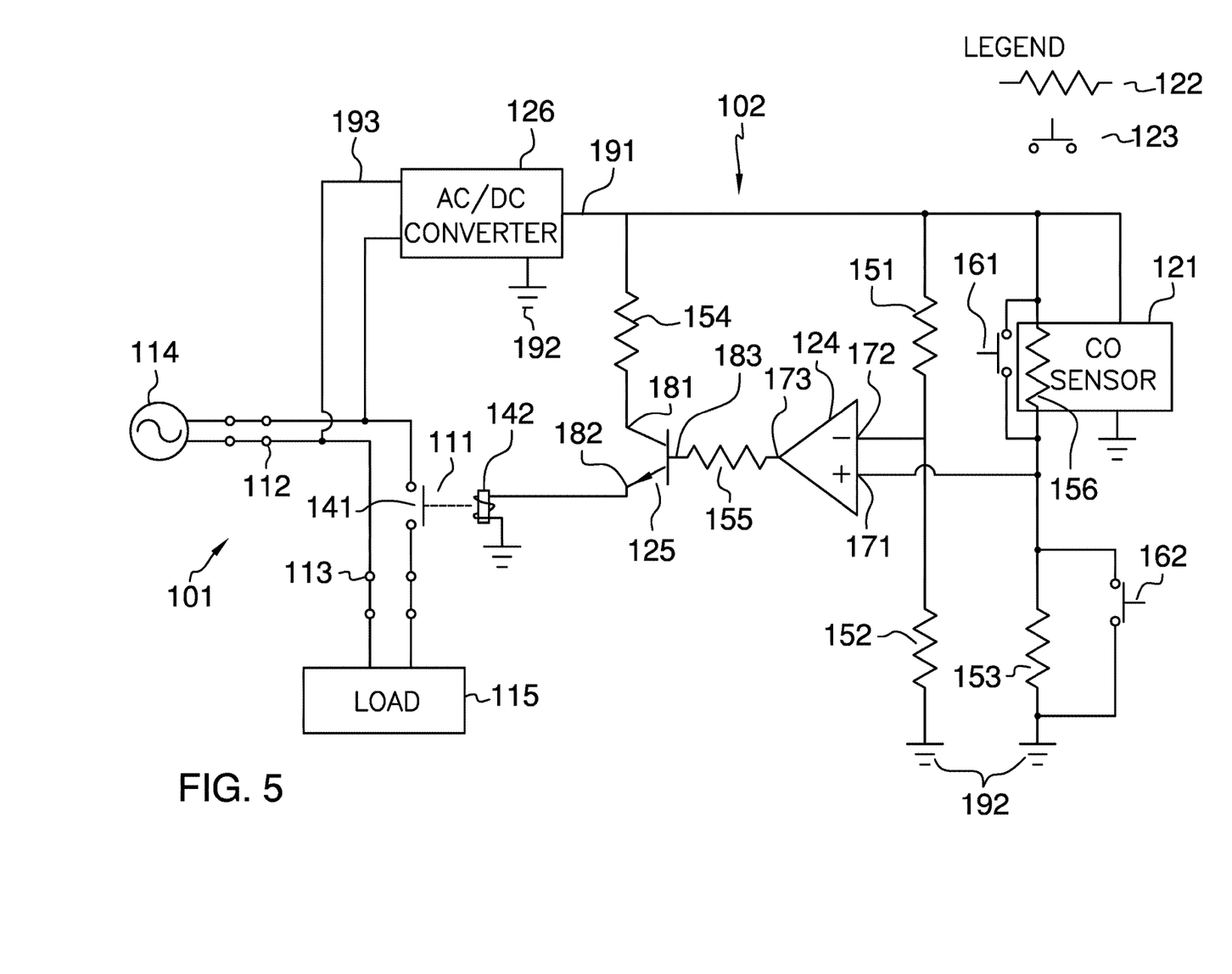
FIG. 5 is a schematic view of an embodiment of the disclosure.

The pass-through circuit 101 is an electrical circuit inserted between the national electric grid 114 and the electrical load 115. The pass-through circuit 101 transports electricity from the national electric grid 114 to the electrical load 115. The pass-through circuit 101 is a switched circuit. The pass-through circuit 101 interrupts the flow of electricity from the national electric grid 114 to the electrical load 115 when carbon monoxide is detected by the control circuit 102. The control circuit 102 operates the pass-through circuit 101. The operating assumption of the invention 100 is that the pass-through circuit 101 controls the flow of electricity into an electrical load 115 that is figured to support a combustion-based chemical reaction. The presence of a high concentration of carbon monoxide indicates a problem with the combustion reaction. The pass-through circuit rectifies this problem by stopping the flow of electricity into the electrical load 115.

The pass-through circuit 101 comprises a relay 111, a NEMA 5-15P electrical plug 112, a NEMA 5-15 electrical socket 113, a national electric grid 114, and an electrical load 115. The relay 111, the NEMA 5-15P electrical plug 112, the NEMA 5-15 electrical socket 113, the national electric grid 114, and the electrical load 115 are electrically interconnected.

The relay 111 is a commercially available relay 111. The relay 111 is a switching device that controls the flow of electricity from the NEMA 5-15P electrical plug 112 to the NEMA 5-15 electrical socket 113. The use of a relay 111 is well-known and documented in the electrical arts. The relay 111 is described in greater detail elsewhere in this disclosure. The relay 111 comprises a relay 111 switch 141 and a relay 111 coil 142.

The relay 111 switch 141 is the switching element of the relay 111. The relay 111 switch 141 is a normally closed switch. The relay 111 switch 141 inserts in series between the NEMA 5-15P electrical plug 112 and the NEMA 5-15 electrical socket 113 such that the relay 111 switch 141 will physically control the flow of electricity between the national electric grid 114 and the electrical load 115. The relay 111 switch 141 is defined in greater detail elsewhere in this disclosure.

The relay 111 coil 142 is the coil of the relay 111 that controls the operation of the relay 111 switch 141. The transistor 125 energizes the relay 111 coil 142. The relay 111 coil 142 is defined in greater detail elsewhere in this disclosure.

The NEMA 5-15P electrical plug 112 is a commercially available electrical plug. The NEMA 5-15P electrical plug 112 electrically connects the pass-through circuit 101 to the national electric grid 114. The NEMA 5-15 electrical socket 113 is a commercially available electrical socket. The NEMA 5-15 electrical socket 113 electrically connects the pass-through circuit 101 to the electrical load 115.

The national electric grid 114 is a commercially available source of AC electrical power. An appropriate authority regulates the national electric grid 114. The national electric grid 114 sells electrical power for use by an electrical load 115. The national electric grid 114 invoices for electrical power based on the total energy consumed by the electrical load 115. The national electric grid 114 measure the energy consumption of an electrical load 115 with an electrical meter. The electrical load 115 is an electrical device designed to connect to the national electric grid 114. This disclosure assumes that the electrical load 115 supports a combustion-based chemical reaction.

The control circuit 102 is an electrical circuit. The control circuit 102 triggers the interruption of the circuit formed by the pass-through circuit 101 when an excessive concentration of carbon monoxide is detected by the control circuit 102. The control circuit 102 comprises a CO sensor 121, a plurality of resistors 122, a plurality of switches 123, an amplifier 124, a transistor 125, and an AC/DC converter 126. The CO sensor 121, the plurality of resistors 122, the plurality of switches 123, the amplifier 124, the transistor 125, and the AC/DC converter 126 are electrically interconnected.

The CO sensor 121 is a commercially available electrical sensor. The CO sensor 121 measures the concentration of carbon monoxide in the atmosphere. The CO sensor 121 further comprises a variable resistor 156. Each of the plurality of resistors 122 is a commercially available resistor. Each of the plurality of resistors 122 are used to control the voltages and currents within the control circuit 102. Each of the plurality of switches 123 is a commercially available electrical switch. The plurality of resistors 122 comprises a first resistor 151, a second resistor 152, a third resistor 153, a fourth resistor 154, and a fifth resistor 155.

The first resistor 151 and the second resistor 152 are electrically connected to form a voltage divider. The first resistor 151 and the second resistor 152 forms a series connection between the second positive terminal 191 and the electrical ground 192. The voltage between the first resistor 151 and the second resistor 152 forms the reference voltage. The reference voltage electrically connects to the first negative terminal 172 of the amplifier 124.

The variable resistor 156 is a resistance that is provided by the CO sensor 121. The value of the resistance presented by the variable resistor 156 is a negative function of the concentration of carbon monoxide that is measured by the CO sensor 121. Specifically, the resistance presented by the variable resistor 156 decreases as the concentration of carbon monoxide increases. The third resistor 153 and the variable resistor 156 are electrically connected to form a voltage divider. The third resistor 153 and the variable resistor 156 forms a series connection between the second positive terminal 191 and the electrical ground 192. The voltage between the third resistor 153 and the variable resistor 156 forms the generated voltage.

The voltage divider formed by the variable resistor 156 and the third resistor 153 operates as follows: a) as carbon monoxide is detected by the CO sensor 121, the resistance of the variable resistor 156 decreases; b) because the voltage generated at the second positive terminal 191 of the AC/DC converter 126 remains constant, the natural response of the voltage divider structure causes the voltage across the third resistor 153 to increase; and, therefore, c) the voltage across the third resistor 153 electrically connects to the first positive terminal 171 of the amplifier 124 to form the generated voltage.

The fourth resistor 154 is a limit resistor that limits the flow of electricity from the second positive terminal 191 of the AC/DC converter 126 into the collector 181 of the transistor 125. The fifth resistor 155 is a limit resistor that limits the flow of electricity from the amplifier 124 output 173 of the amplifier 124 into the base 183 of the transistor 125.

The plurality of switches 123 performs a function selected from the group consisting of: a) testing the operation of the invention 100; and, b) resetting the pass-through circuit 101 to allow for the flow of electricity from the national electric grid 114 to the electrical load 115. The plurality of switches 123 comprises a test switch 161 and a reset switch 162. The test switch 161 is a momentary switch. The test switch 161 connects in parallel across the variable resistor 156 of the CO sensor 121. When the test switch 161 closes, the test switch 161 shorts out the variable resistor 156 which causes the amplifier 124 to energize the relay 111 coil 142. The reset switch 162 connects in parallel across the third resistor 153.

When the reset switch 162 closes, the reset switch 162 shorts out the third resistor 153 which causes the amplifier 124 to discontinue the operation of the relay 111 coil 142.

The amplifier 124 is a commercially available electrical device that: 1) amplifies a control signal generated by the CO sensor 121 which drives the transistor 125; and, 2) electrically buffers the CO sensor 121 from voltage spikes generated by the transistor 125. The amplifier 124 is a differential amplifier commonly referred to as an operational amplifier. The amplifier 124 forms a comparator circuit that compares a reference voltage to a generated voltage. The generated voltage is a voltage that varies as a function of the carbon monoxide concentration measured by the CO sensor 121. When the generated voltage exceeds the reference voltage, the amplifier 124 generates a voltage signal to the transistor 125 that powers the relay 111 coil 142. The amplifier 124 further comprises a first positive terminal 171, a first negative terminal 172, and an amplifier 124 output 173.

The first positive terminal 171 is an input lead of the amplifier 124. The first negative terminal 172 is an input lead of the amplifier 124. The amplifier 124 output 173 generates an output voltage that is proportional to the difference between the first positive terminal 171 and the first negative terminal 172. The amplifier 124 output 173 generates a positive voltage when the voltage presented at the first positive terminal 171 is greater than the voltage presented at the first negative terminal 172. The amplifier 124 output 173 generates a negative voltage when the voltage presented at the first positive terminal 171 is lesser than the voltage presented at the first negative terminal 172.

The transistor 125 operates as a switch. The transistor 125 further comprises a collector 181, an emitter 182, and a base 183. When a voltage is applied to the base 183, current will flow into the base 183 and the transistor 125 will act like a closed switch allowing current to flow from the collector 181 to the emitter 182. When the voltage is removed from the base 183, the transistor 125 will act like an open switch disrupting current flow from the collector 181 to the emitter 182. When the transistor 125 is in the closed state, the transistor 125 provides the electric current required to operate the relay 111 coil 142. The base 183 of the transistor 125 is driven by the amplifier 124 output 173.

The collector 181 is a first switch lead of the transistor 125. The emitter 182 is a second switch lead of the transistor 125. The base 183 is the electrical connection that controls the operation of the transistor 125. When a positive voltage is presented to the base 183, the transistor 125 will allow the flow of electricity through the transistor 125 from the collector 181 to the emitter 182 and into the relay 111 coil 142.

The AC/DC converter 126 is an electrical circuit. The AC/DC converter 126 draws AC electrical power from the NEMA 5-15P electrical plug 112 and converts the drawn power into DC electrical energy used to operate the control circuit 102 and the relay 111 coil 142. The use and design of an AC/DC converter 126 are well-known and documented in the electrical arts. The AC/DC converter 126 is a commercially available device. The AC/DC converter 126 further comprises a second positive terminal 191, an electrical ground 192, and a power tap 193. The second positive terminal 191 is the positive DC output of the AC/DC converter 126. The electrical ground 192 is provisioned by the AC/DC converter 126 to form the electrical ground 192 of the control circuit 102. The power tap 193 refers to the electrical connection between the AC/DC converter 126 and the NEMA 5-15P electrical plug 112.

Figure 1:
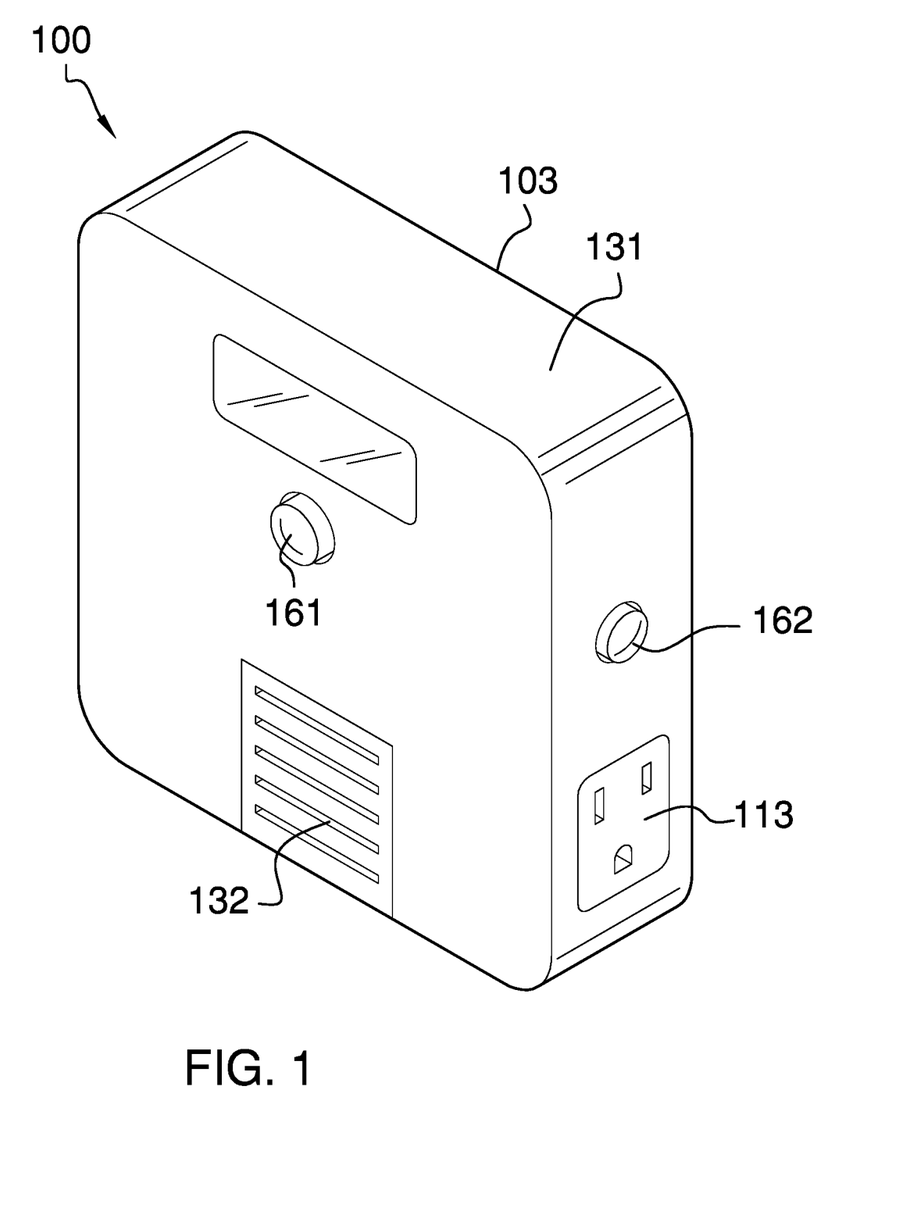
FIG. 1 is a perspective view of an embodiment of the disclosure.
Figure 2:
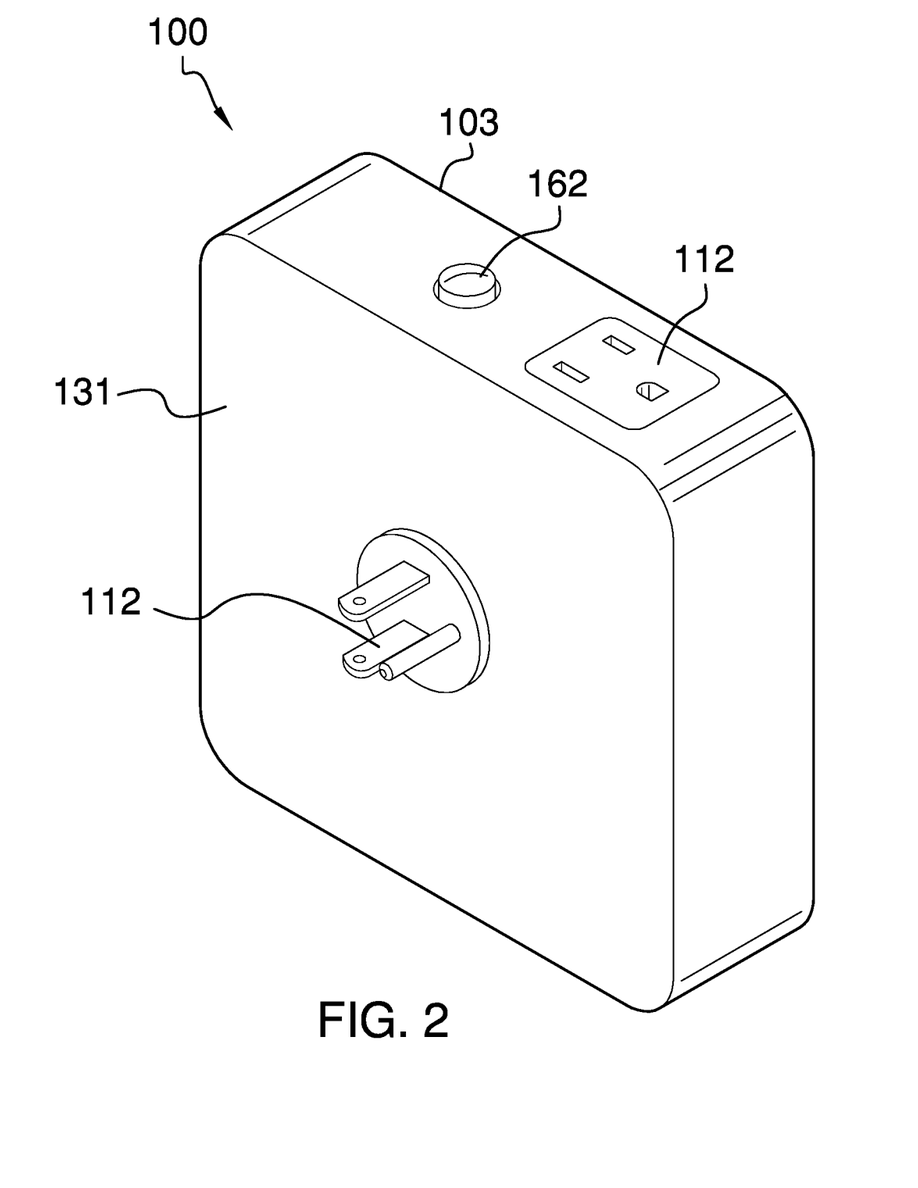
FIG. 2 is a perspective view of an embodiment of the disclosure.
Figure 3:
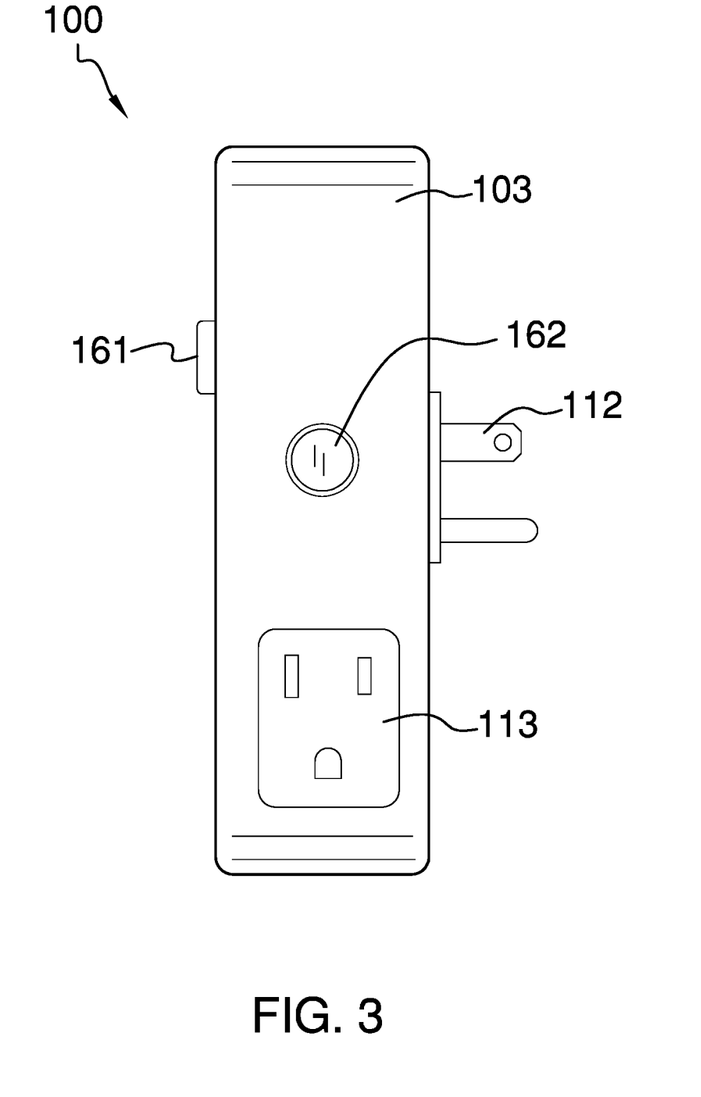
FIG. 3 is a side view of an embodiment of the disclosure.
Figure 4:
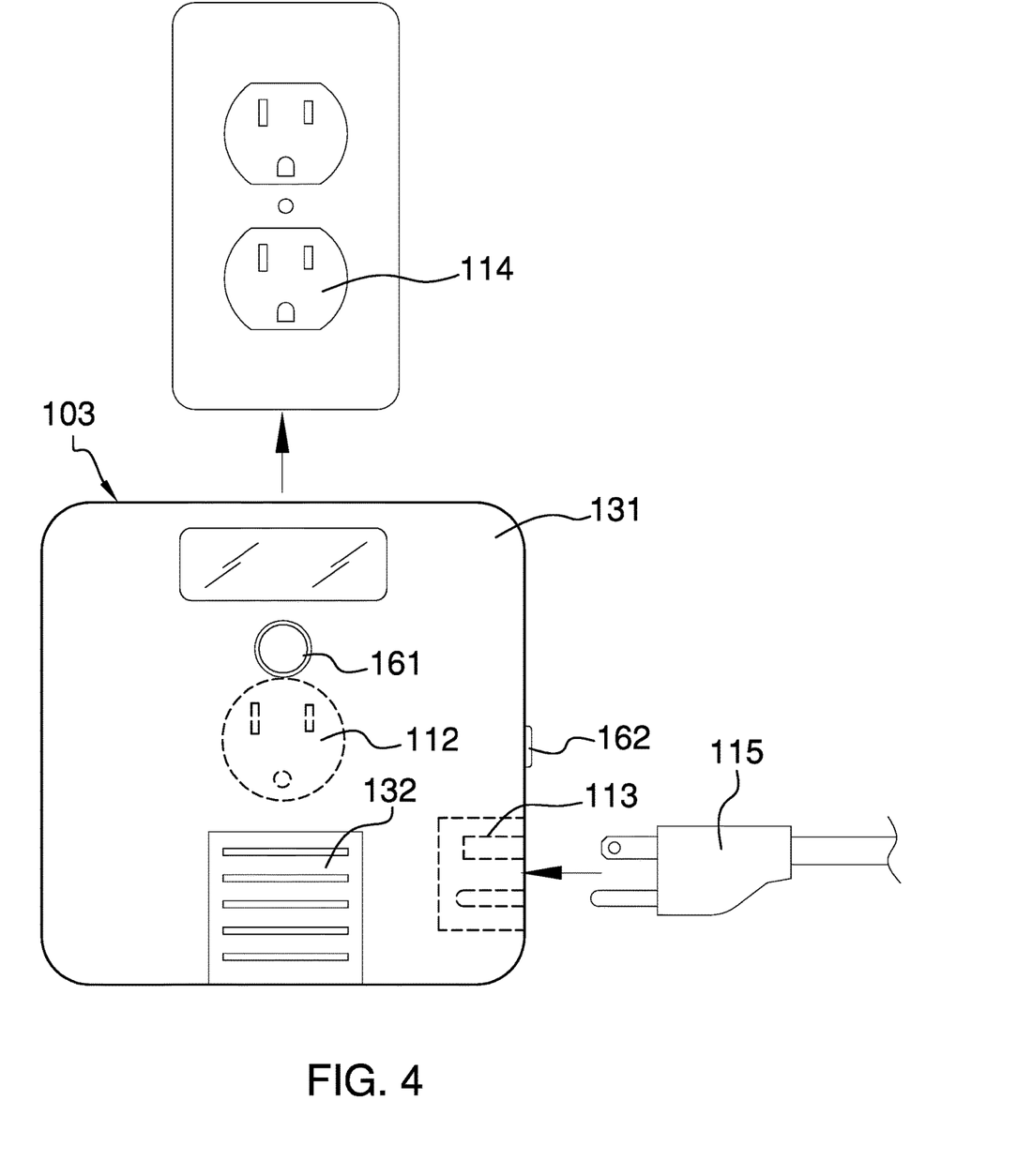
FIG. 4 is an in-use view of an embodiment of the disclosure.

The housing 103 is a containment structure. The housing 103 contains the pass-through circuit 101 and the control circuit 102. The housing 103 is formed with all apertures and form factors necessary to allow the housing 103 to accommodate the use and operation of the invention 100. Methods to form a housing 103 suitable for the purposes described in this disclosure are well-known and documented in the mechanical arts. The housing 103 comprises a case 131 and a vent 132. The case 131 is a rigid enclosure that forms the outer shell of the invention 100. The vent 132 is an aperture formed through the case 131. The vent 132 allows air to flow into and out of the case 131.

The following three paragraphs describe the operation of the invention 100.

In the normal mode of operation, electricity flows freely from the national electric grid 114 and the NEMA 5-15P electrical plug 112 through the relay 111 switch 141 and into the NEMA 5-15 electrical socket 113 and the electrical load 115.

When the CO sensor 121 detects a high concentration of carbon monoxide, the CO sensor 121 reduces the resistance presented by the variable resistor 156 such that the generated voltage presented by the third resistor 153 to the amplifier 124 rises above the reference voltage presented by the second resistor 152 to the amplifier 124. When the generated voltage exceeds the reference voltage, the amplifier 124 enables the transistor 125 to permit the flow of electricity to energize the relay 111 coil 142. Energizing the relay 111 coil 142 causes the relay 111 switch 141 to open which shuts the flow of power into the electrical load 115.

The relay 111 switch 141 remains in the open state until the carbon monoxide concentration detected by the CO sensor 121 reaches a point where the generated voltage falls below the reference voltage.

The following definitions were used in this disclosure:

AC: As used in this disclosure, AC is an acronym for alternating current.

AC/DC Converter: As used in this disclosure, an AC/DC converter is an electrical device that converts an AC voltage into a regulated DC voltage by rectifying and regulating the AC voltage. Method to design and build AC/DC converters are well-known in the electrical arts. The AC/DC converter is further defined with a positive terminal, a negative terminal and a power input.

Amplifier: As used in this disclosure, an amplifier refers to an electronic component that increases voltage, current, or power of an input signal. Specifically, within this disclosure, an amplifier refers to a differential amplifier. A differential amplifier is a device two input electrical device with a single output. A difference amplifier amplifies the voltage difference between the two inputs.

Carbon Monoxide: As used in this disclosure, carbon monoxide (CAS 630-08-0) refers to a chemical compound with the formula CO.

DC: As used in this disclosure, DC is an acronym for direct current.

Electrical Ground: As used in this disclosure, an electrical ground is a common reference voltage used in the design and implementation of electrical circuits. An electrical ground is often, but not necessarily, the discharge point of electric currents flowing through an electric circuit.

Form Factor: As used in this disclosure, the term form factor refers to the size and shape of an object.

Housing: As used in this disclosure, a housing is a rigid casing that encloses and protects one or more devices.

Limit Resistor: As used in this disclosure, a limit resistor is an electrical resistor that is used to limit the flow of electric current through an electrical circuit.

Load: As used in this disclosure, the term load refers to an object upon which a force is acting or which is otherwise absorbing energy in some fashion. Examples of a load in this sense include, but are not limited to, a mass that is being moved a distance or an electrical circuit element that draws energy. The term load is also commonly used to refer to the forces that are applied to a stationary structure.

Momentary Switch: As used in this disclosure, a momentary switch is a biased switch in the sense that the momentary switch has a baseline position that only changes when the momentary switch is actuated (for example when a pushbutton switch is pushed or a relay coil is energized). The momentary switch then returns to the baseline position once the actuation is completed. This baseline position is called the "normal" position. For example, a "normally open" momentary switch interrupts (open) the electric circuit in the baseline position and completes (closes) the circuit when the momentary switch is activated. Similarly, a "normally closed" momentary switch will complete (close) an electric circuit in the baseline position and interrupt (open) the circuit when the momentary switch is activated.

National Electric Grid: As used in this disclosure, the national electric grid is a synchronized and highly interconnected electrical network that distributes energy in the form of electric power from a plurality of generating stations to consumers of electricity.

NEMA: As used in this disclosure, NEMA is an acronym for National Electric Manufacturers Association. NEMA is a manufacturer's association known for publishing widely accepted technical standards regarding the performance of electrical power distribution equipment.

NEMA 5-15 Electrical Socket: As used in this disclosure, the NEMA 5-15 electrical socket is a port designed to provide electric power drawn from the National Electric Grid. The NEMA 5-15 electrical socket is commonly used to deliver electrical power to electric devices in residential, office, and light industrial settings. The typical NEMA5-15 electrical socket comprises a plurality of electric ports from which electric power is drawn. The position of each of the plurality of electric ports is placed in a standardized position. The typical NEMA5-15 electrical socket further comprises a plate hole which is a standardized hole located in a standardized position within the NEMA 5-15 electrical socket that that is designed to receive a bolt that is used to attach a faceplate to the NEMA 5-15 electrical socket. The NEMA 5-15 electrical socket is also commonly referred to as an electrical outlet.

NEMA 5-15P Electrical Plug: As used in this disclosure, the NEMA 5-15P Electrical Plug is a plug that is designed to be inserted into a NEMA 5-15 Electrical Socket for the purpose of delivering electrical power to electrical devices. The NEMA 5-15P Electrical Plug is a three blade plug commonly found within residential and office environments within the United States.

Normally Closed: As used in this disclosure, normally closed refers to an externally controlled electrical switching device, such as a relay or a momentary switch, which passes electric current when the externally controlled electrical switching device is unpowered.

Normally Open: As used in this disclosure, normally open refers to an externally controlled electrical switching device, such as a relay or a momentary switch, which does not pass electric current when the externally controlled electrical switching device is unpowered.

Plug: As used in this disclosure, a plug is an electrical termination that electrically connects a first electrical circuit to a second electrical circuit or a source of electricity. As used in this disclosure, a plug will have two or three metal pins.

Relay: As used in this disclosure, a relay is an automatic electromagnetic or electromechanical device that reacts to changes in voltage or current by opening or closing a switch in an electric circuit. Relays further defined with a coil and a switch. Applying a voltage to the coil, usually referred to as energizing the coil, will cause the coil to change the position of the switch. Note: Though transistors can be configured to perform switching functions, transistors used for switching functions are handled separately in this disclosure and are explicitly excluded from this definition.

Resistor: As used in this disclosure, a resistor is a well-known and commonly available electrical device that inhibits the flow of electricity through an electric circuit. Within an electric circuit processing alternating currents, the resistor will not affect the phase of the alternating current. A current flowing through a resistor will create a voltage across the terminals of the resistor.

Sensor: As used in this disclosure, a sensor is a device that receives and responds in a predetermined way to a signal or stimulus. As further used in this disclosure, a threshold sensor is a sensor that generates a signal that indicates whether the signal or stimulus is above or below a given threshold for the signal or stimulus.

Socket: As used in this disclosure, a socket is an electrical device that 1) forms an opening or a cavity that acts as a receptacle for an inserted object; and 2) is designed to receive or transfer electricity to or from the object inserted in the socket.

Switch: As used in this disclosure, a switch is an electrical device that starts and stops the flow of electricity through an electric circuit by completing or interrupting an electric circuit. The act of completing or breaking the electrical circuit is called actuation. Completing or interrupting an electric circuit with a switch is often referred to as closing or opening a switch respectively. Completing or interrupting an electric circuit is also often referred to as making or breaking the circuit respectively.

Transistor: As used in this disclosure, a transistor is a general term for a three-terminal semiconducting electrical device used for electrical signal amplification and electrical switching applications. There are several designs of transistors. A common example of a transistor is an NPN transistor that further comprises a collector terminal, an emitter terminal, and a base terminal and which consists of a combination of two rectifying junctions (a diode is an example of a rectifying junction). Current flowing from the collector terminal through the emitter terminal crosses the two rectifier junctions. The amount of the electric current crossing the two rectified junctions is controlled by the amount of electric current that flows through the base terminal. This disclosure assumes the use of an NPN transistor. This assumption is made solely for the purposes of simplicity and clarity of exposition. Those skilled in the electrical arts will recognize that other types of transistors, including but not limited to, field effect transistors and PNP transistors, can be substituted for an NPN transistor without undue experimentation.

Vent: As used in this disclosure, a vent is an opening in a structure that allows for the flow of gas through the boundary of the structure.

With respect to the above description, it is to be realized that the optimum dimensional relationship for the various components of the invention described above and in FIGS.

1 through 5 include variations in size, materials, shape, form, function, and manner of operation, assembly and use, are deemed readily apparent and obvious to one skilled in the art, and all equivalent relationships to those illustrated in the drawings and described in the specification are intended to be encompassed by the invention.

It shall be noted that those skilled in the art will readily recognize numerous adaptations and modifications which can be made to the various embodiments of the present invention which will result in an improved invention, yet all of which will fall within the spirit and scope of the present invention as defined in the following claims. Accordingly, the invention is to be limited only by the scope of the following claims and their equivalents.

The inventors claim:

1. A carbon monoxide detector and shutoff system comprising:
a pass-through circuit, a control circuit, and a housing;
wherein the housing contains the pass-through circuit and the control circuit;
wherein the carbon monoxide detector and shutoff system is an electrical switching device;
wherein the carbon monoxide detector and shutoff system inserts into an electrical connection between a national electric grid and an electrical load;
wherein the carbon monoxide detector and shutoff system senses the carbon monoxide concentration within the atmosphere;
wherein the carbon monoxide detector and shutoff system interrupts the circuit between the national electric grid and the electrical load when the detected concentration of carbon monoxide exceeds a threshold level;
wherein the pass-through circuit transports electricity from the national electric grid to the electrical load;
wherein the pass-through circuit is a switched circuit;
wherein the pass-through circuit inserts between the national electric grid and the electrical load;
wherein the control circuit is an electrical circuit that operates the pass-through circuit in response to the detected concentration of carbon monoxide;
wherein the control circuit operates the pass-through circuit;
wherein the pass-through circuit interrupts the flow of electricity from the national electric grid to the electrical load when the control circuit detects carbon monoxide;
wherein the pass-through circuit comprises a relay, a NEMA 5-15p electrical plug, a NEMA 5-15 electrical socket, a national electric grid, and an electrical load;
wherein the relay, the NEMA 5-15p electrical plug, the NEMA 5-15 electrical socket, the national electric grid, and the electrical load are electrically interconnected;
wherein the relay comprises a relay switch and a relay coil;
wherein the relay switch is the switching element of the relay;
wherein the relay switch is a normally closed switch;
wherein the relay coil controls the operation of the relay switch;
wherein the relay switch inserts in series between the NEMA 5-15p electrical plug and the NEMA 5-15 electrical socket such that the relay switch will physically control the flow of electricity between the national electric grid and the electrical load;
wherein the control circuit energizes the relay coil;
wherein the control circuit comprises a CO sensor, a plurality of resistors, a plurality of switches, an amplifier, a transistor, and an AC/DC converter;
wherein the CO sensor, the plurality of resistors, the plurality of switches, the amplifier, the transistor, and the AC/DC converter are electrically interconnected.

2. The carbon monoxide detector and shutoff system according to claim 1
wherein the NEMA 5-15p electrical plug electrically connects the pass-through circuit to the national electric grid;
wherein the NEMA 5-15 electrical socket electrically connects the pass-through circuit to the electrical load.

3. The carbon monoxide detector and shutoff system according to claim 2
wherein the CO sensor is an electrical sensor;
wherein the CO sensor measures the concentration of carbon monoxide in the atmosphere.

4. The carbon monoxide detector and shutoff system according to claim 3
wherein the CO sensor further comprises a variable resistor;
wherein the variable resistor is a resistance that is provided by the CO sensor;
wherein the value of the resistance presented by the variable resistor is a negative function of the concentration of carbon monoxide that is measured by the CO sensor.

5. The carbon monoxide detector and shutoff system according to claim 4
wherein the plurality of resistors comprises a first resistor, a second resistor, a third resistor, a fourth resistor, and a fifth resistor;
wherein each of the plurality of resistors is used to control the voltages and currents within the control circuit.

6. The carbon monoxide detector and shutoff system according to claim 5
wherein the first resistor and the second resistor forms a series connection;
wherein the first resistor and the second resistor are electrically connected to form a voltage divider;
wherein the voltage between the first resistor and the second resistor forms a reference voltage.

7. The carbon monoxide detector and shutoff system according to claim 6
wherein the third resistor and the variable resistor forms a series connection;
wherein the third resistor and the variable resistor are electrically connected to form a voltage divider;
wherein the voltage between the third resistor and the variable resistor forms a generated voltage.

8. The carbon monoxide detector and shutoff system according to claim 7
wherein the fourth resistor is a limit resistor that limits the flow of electricity from the second positive terminal of the AC/DC converter into the collector of the transistor;
wherein the fifth resistor is a limit resistor that limits the flow of electricity from the amplifier output of the amplifier into the base of the transistor.

9. The carbon monoxide detector and shutoff system according to claim 8
wherein the plurality of switches comprises a test switch and a reset switch;
wherein the test switch is a momentary switch;
wherein the test switch electrically connects in parallel across the variable resistor of the CO sensor;

wherein the test switch shorts out the variable resistor when closed;

wherein the reset switch electrically connects in parallel across the third resistor;

wherein the reset switch shorts out the third resistor when closed.

10. The carbon monoxide detector and shutoff system according to claim 9
wherein the amplifier amplifies a control signal generated by the CO sensor;
wherein the amplifier drives the transistor.

11. The carbon monoxide detector and shutoff system according to claim 10
wherein the amplifier is a differential amplifier;
wherein the amplifier further comprises a first positive terminal, a first negative terminal, and an amplifier output;
wherein the first positive terminal is an input lead of the amplifier;
wherein the first negative terminal is an input lead of the amplifier;
wherein the amplifier output generates an output voltage that is proportional to the difference between the first positive terminal and the first negative terminal;
wherein the amplifier output generates a positive voltage when the voltage presented at the first positive terminal is greater than the voltage presented at the first negative terminal;
wherein the amplifier output generates a negative voltage when the voltage presented at the first positive terminal is lesser than the voltage presented at the first negative terminal;
wherein the reference voltage electrically connects to the first negative terminal of the amplifier;
wherein the generated voltage electrically connects to the first positive terminal of the amplifier.

12. The carbon monoxide detector and shutoff system according to claim 11
wherein the amplifier forms a comparator circuit that compares the reference voltage to the generated voltage;
wherein the generated voltage is a voltage that varies as a function of the carbon monoxide concentration measured by the CO sensor;
wherein when the generated voltage exceeds the reference voltage the amplifier generates a voltage signal to the transistor that powers the relay coil.

13. The carbon monoxide detector and shutoff system according to claim 12
wherein the transistor operates as a switch;
wherein the transistor further comprises a collector, an emitter, and a base;
wherein when a voltage is applied to the base, current will flow into the base and the transistor will act like a closed switch allowing current to flow from the collector to the emitter;
wherein when the voltage is removed from the base, the transistor will act like an open switch disrupting current flow from the collector to the emitter;
wherein when the transistor is in the closed state, the transistor provides the electric current required to operate the relay coil;
wherein the base of the transistor is driven by the amplifier output;
wherein when a positive voltage is presented to the base, the transistor will allow the flow of electricity through the transistor from the collector to the emitter and into the relay coil.

14. The carbon monoxide detector and shutoff system according to claim 13
wherein the AC/DC converter is an electrical circuit;
wherein the AC/DC converter draws AC electrical power from the NEMA 5-15p electrical plug and converts the drawn power into DC electrical energy used to operate the control circuit and the relay coil;
wherein the AC/DC converter further comprises a second positive terminal, an electrical ground, and a power tap;
wherein the second positive terminal is the positive DC output of the AC/DC converter;
wherein the electrical ground is provisioned by the AC/DC converter to form the electrical ground of the control circuit;
wherein the power tap is the electrical connection between the AC/DC converter and the NEMA 5-15p electrical plug;
wherein the first resistor and the second resistor forms a series connection between the second positive terminal and the electrical ground;
wherein the third resistor and the variable resistor forms a series connection between the second positive terminal and the electrical ground.

15. The carbon monoxide detector and shutoff system according to claim 14
wherein the housing is a containment structure;
wherein the housing comprises a case and a vent;
wherein the case is a rigid enclosure that forms the outer shell of the carbon monoxide detector and shutoff system;
wherein the vent is an aperture formed through the case;
wherein the vent allows air to flow into and out of the case.

* * * * *